United States Patent [19]
Wang

[11] Patent Number: 5,273,633
[45] Date of Patent: Dec. 28, 1993

[54] CAPILLARY MULTIREFLECTIVE CELL

[76] Inventor: Tiansong Wang, 10 Hamilton Rd., Chapel Hill, N.C. 27514

[21] Appl. No.: 911,607

[22] Filed: Jul. 10, 1992

[51] Int. Cl.$^5$ .................... G01N 27/26; G01N 27/447
[52] U.S. Cl. .............................. 204/180.1; 204/299 R; 356/246; 356/344
[58] Field of Search ................. 73/61.58, 61.57, 61.53, 73/61.52; 356/246, 344; 204/180.1, 299 R

[56] References Cited

U.S. PATENT DOCUMENTS

| | | | |
|---|---|---|---|
| 3,418,053 | 12/1968 | Pelavin | 356/246 X |
| 3,431,424 | 3/1969 | Allen | 356/337 X |
| 3,999,861 | 12/1976 | Bellinger | 356/246 X |
| 4,690,560 | 1/1987 | Coogan | 356/246 X |

OTHER PUBLICATIONS

Xiaobing Xi and Edward S. Yeung "Axial-Beam On-Column Absorption Detection for Open Tubular Capillary Liquid Chromatography" Analytical Chemistry, vol. 62, No. 15 (1990) 1580–1584.
Takao Tsuda, Jonathan V. Sweedler, and Richard N. Zare "Rectangular Capillaries for Capillary Zone Electrophoresis" Analytical Chemistry, vol. 62, No. 19 (1990) 2149–2152.
Philip L. Hanst "Spectroscopic Methods for Air Pollution Measurement" Advances in Environmental Science and Technology, vol. 2 edited by James N. Pitts, Jr. and Robert L. Metcalf (1971) 91–165.

*Primary Examiner*—John Niebling
*Assistant Examiner*—John S. Starsiak, Jr.
*Attorney, Agent, or Firm*—Salzman & Levy

[57] ABSTRACT

The present invention features a system for detecting a substance in a fluid sample. A capillary is provided with a longitudinal axis and a channel is formed in it for receiving a fluid sample. The channel is disposed parallel to the longitudinal axis. A reflecting surface surrounds the outer surface of the capillary for reflecting electromagnetic energy. The reflecting surface has an incident window for allowing the electromagnetic energy to enter the capillary and an exit window for allowing the electromagnetic energy to exit the capillary. The exit window is disposed downstream of the incident window with respect to the longitudinal axis, so that the electromagnetic energy that enters the capillary is internally reflected more than once by the reflecting surface.

10 Claims, 12 Drawing Sheets

CAPILLARY MULTIREFLECTIVE CELL

BACKGROUND OF THE INVENTION

The present invention relates to a system for analyzing substances by using capillary zone electrophoresis (CZE) and, more particularly, to CZE systems using a multireflective cell.

When determining the composition of a substance through light absorption detection, photons are passed through the substance; that portion of energy not absorbed is thus detected. Energy spectra not absorbed by the substance can be used for at least two purposes: (1) to indicate the composition of an unknown substance; and (2) to determine the presence and/or quantity of a predetermined material (e.g., element, molecule, etc.) in the substance.

Capillary zone electrophoresis (CZE) is such a system for performing this analysis. To assess a substance, a sample is drawn through a long, transparent capillary by the process of electrophoresis (the movement of suspended particles through a fluid via an electromotive force). Electromagnetic energy (e.g., a laser beam or ultraviolet light) is passed through the transparent capillary. Energy is partially absorbed by the sample within the capillary. The energy not absorbed by the sample is detected by a photodetector. The detection can be performed whether the sample in the capillary is stationary or moving.

Detection is one of the most important areas of CZE. Various principles, such as those employed in spectrophotometric, mass spectrometric, electrochemical and radiometric detection, have been applied to CZE. Although the sensitivity of UV-visible absorption detection is perhaps the least among these detection methods, UV detectors are the most frequently used in CZE because of their simplicity and versatility.

Most CZE systems employ a single-pass detection technique, wherein electromagnetic energy passes once through the sample, and the light beam travels normal to the capillary axis, crossing the capillary only a single time. According to Beer's law, $$A = \epsilon \cdot b \cdot c$$

where A is absorbance, $\epsilon$ is molar absorptivity of the sample, b is path length of the electromagnetic energy and c is sample concentration.

The CZE technique is successful only when the sample is thin enough for a sufficient dissipation of heat. Thus, CZE analysis is conducted on a small scale (e.g., a sample is typically 50-75 $\mu$m thick). In single-pass detection, sensitivity is minimal because the path length is limited by the thickness of the sample. Therefore, even with state-of-the-art detectors, concentration detection limits are rarely lower than $10^{-6}$M.

For a given molecule in a particular separation environment, absorption detection limits can be improved by decreasing the noise and/or increasing the path length. Some UV detectors for CZE have noise levels as low as $2 \times 10^{-5}$ au, resulting in detection limits on the order of $10^{-6}$M. The detection limit can also be improved by increasing the effective path length. In "Rectangular Capillaries for Capillary Zone Electrophoresis", Tsuda, T.; Sweedler, J. V.; Zare, R. N. *Analytical Chemistry* 1990, 62, 2149-2152, rectangular capillaries have been investigated for CZE. Using the rectangular capillary, a 20-fold increase in path length and a 15-fold increase in sensitivity was obtained. The increase in detection sensitivity was due to the wider dimension.

A "z"-shaped absorption cell has also been developed for capillary liquid chromatography, which significantly enhances path length and detection sensitivity. This seems promising, but the volume of the z-shaped cell is too large for CZE.

Axial-beam absorption detection was introduced in "Axial-Beam On-Column Absorption Detection for Open Tubular Capillary Liquid Chromatography", Xi, X.; Yeung, E. S. *Analytical Chemistry* 1990, 62, 1580-1585. A beam of light was introduced into a capillary along its major axis. The light beam struck the sample within the capillary. Light that was not absorbed exited from the end of the capillary and was detected. Axial-beam detection requires precise alignment of the capillary and the light source; it also restricts the choice of mobile phase to solutions with refractive indices higher than that of fused silica.

The "White cell" is referred to in "Spectroscopic Methods For Air Pollution Measurement", White, J. U. J. *Advances in Environmental Science and Technology* 1971, 32, 285-288. The White cell contained mirrors within the actual cell itself. The cell increased effective path length using multireflection by these mirrors. This effectively increased the sensitivity of absorption detection. However, this cell is too large for CZE purposes. It can be used only for analysis of low-level gaseous substances.

It would be advantageous to apply a multireflection technique to increase path length to CZE and, therefore, increase detection sensitivity.

It would also be advantageous to increase path length without increasing capillary size.

It would further be advantageous to create a system that is compatible with the standard CZE system in the industry.

It would further be advantageous to provide means for positioning the capillary cell with respect to an electromagnetic energy source.

It would further be advantageous to provide a reflective mechanism external to the capillary.

SUMMARY OF THE INVENTION

In accordance with the present invention, there is provided a system for detecting a substance in a fluid sample. A capillary is provided with a longitudinal axis; a channel is formed therein for receiving a fluid sample. The channel is disposed parallel to the longitudinal axis. A reflecting surface surrounds the outer surface of the capillary for reflecting electromagnetic energy. The reflecting surface has an incident window for allowing the electromagnetic energy to enter the capillary and an exit window for allowing the electromagnetic energy to exit the capillary. The exit window is disposed downstream of the incident window with respect to the longitudinal axis, so that the electromagnetic energy entering the capillary is internally reflected more than once by the reflecting surface.

BRIEF DESCRIPTION OF THE DRAWINGS

A complete understanding of the present invention may be obtained by reference to the accompanying drawings, when taken in conjunction with the detailed description thereof, and in which.

DETAILED DESCRIPTION OF THE PREFERRED EMBODIMENT

Figure 1A:
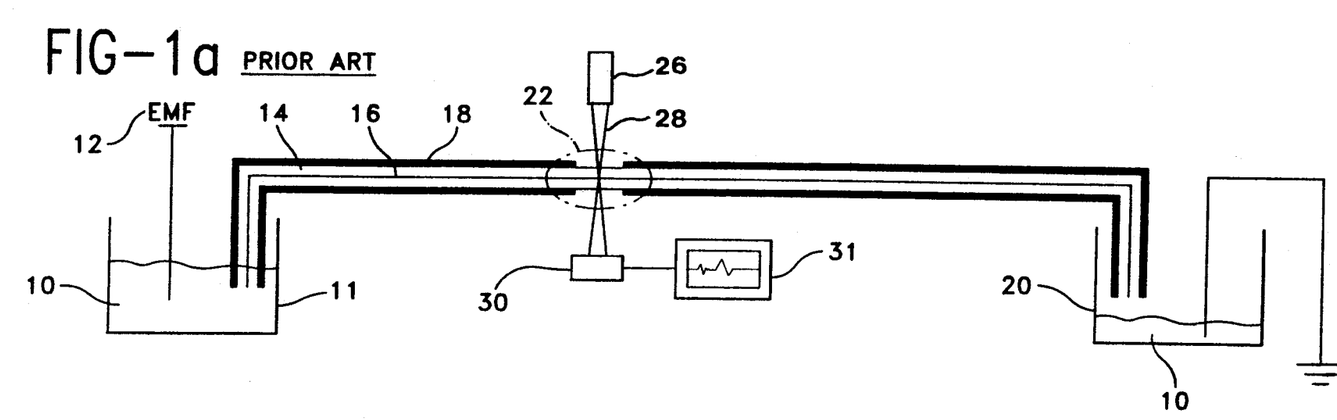
FIGS. 1a and 1b show a typical CZE system of the prior art with an enlarged capillary profile.
Figure 1B:
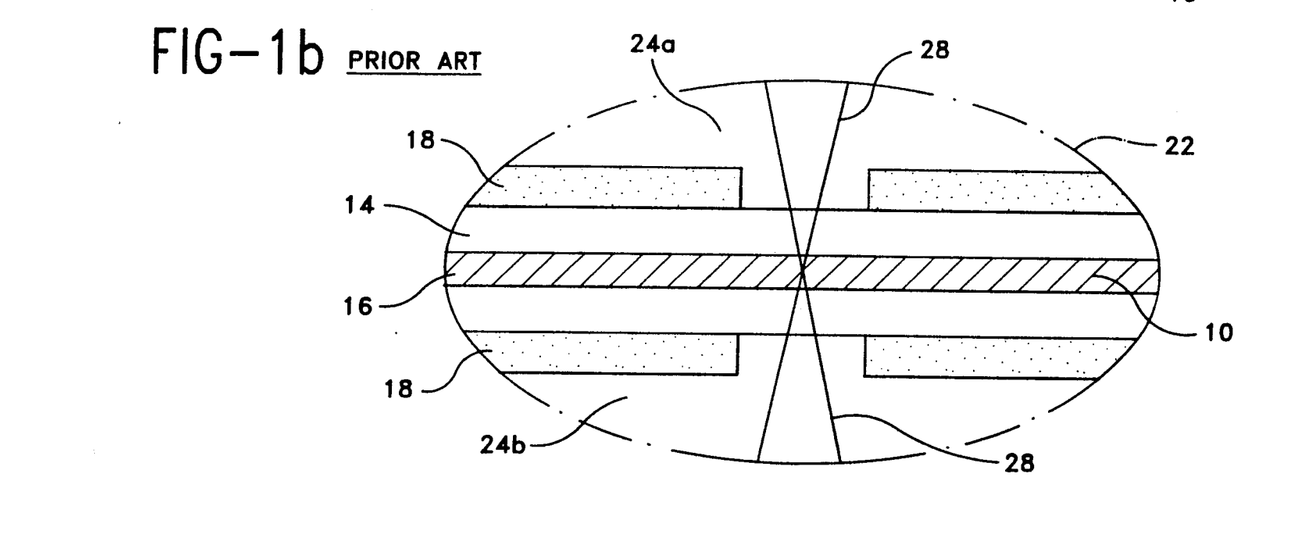

Referring now to FIGS. 1a and 1b there is shown a capillary zone electrophoresis (CZE) device that is typical of those used in prior art systems. A fluid sample 10 resides in a buffer 11. A source of high electromotive force 12 pushes the fluid sample 10 through a longitudinal, transparent capillary 14, via a channel 16 formed therein. A polyimide sleeve 18 is disposed around the outer surface of the capillary 14 for protection thereof. A reservoir 20 catches the fluid 10 as it leaves the capillary 14.

A cell 22, shown in an enlarged cross-section in FIG. 1b, is formed by etching windows 24a and 24b out of the polyimide sleeve 18. A light source 26 (such as a laser) generates a beam of light 28 that passes through the capillary cell 22. The beam of light 28 is partially absorbed by the fluid sample 10 in the channel 16. A photodetector 30 detects light not absorbed by the fluid sample 10. A recording system 31 records data generated by the photodetector 30.

Figure 2:
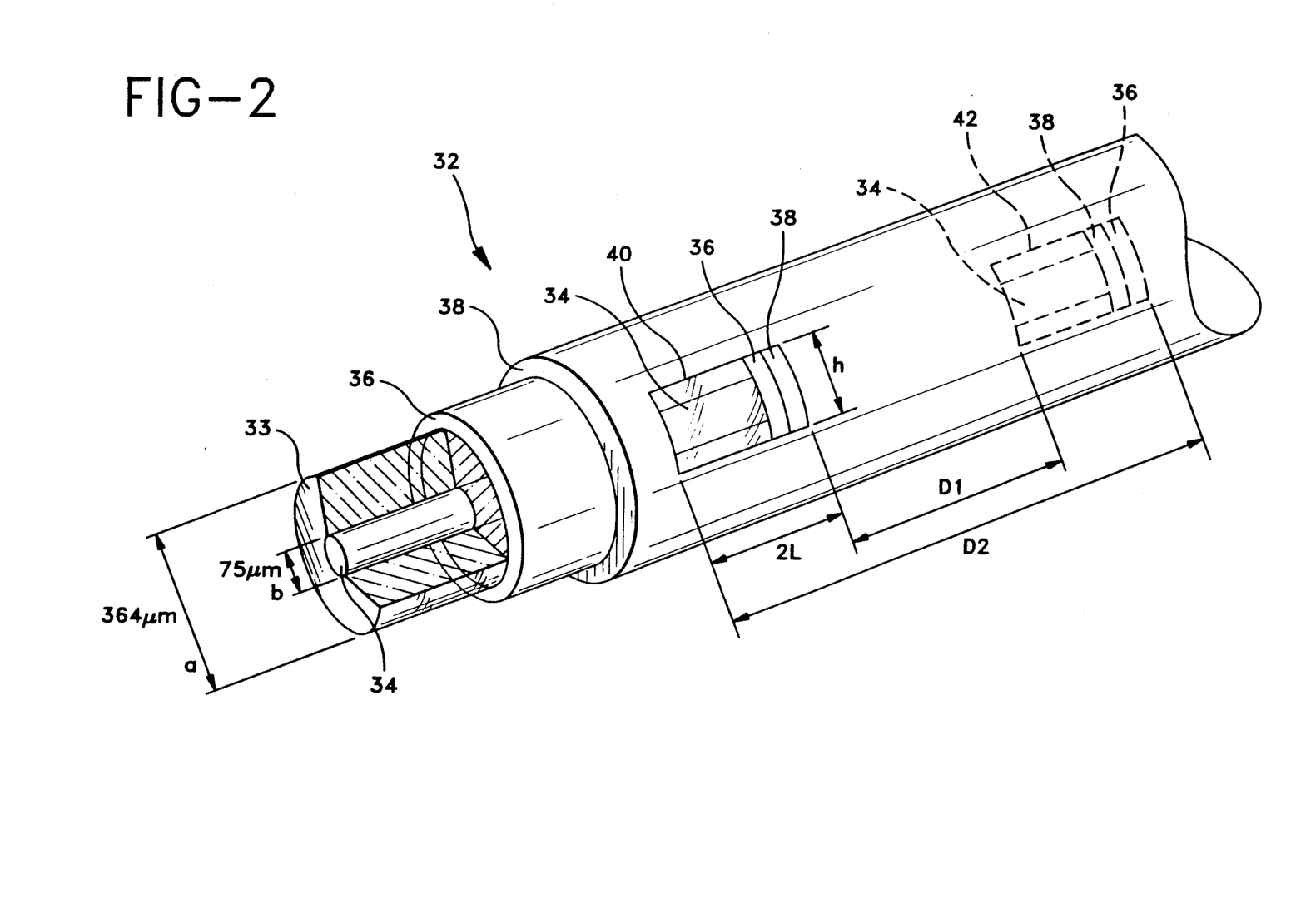
FIG. 2 is a perspective view of the multireflection absorption cell with a cut-away view of the capillary.

Referring now to FIG. 2, there is shown a perspective view of the multireflective cell 32 in accordance with the present invention. A transparent capillary 33 is made of fused silica with an outer diameter of 364 μm in the preferred embodiment. The length of the capillary 33 is 51 cm in the preferred embodiment. A channel 34 carries fluid (not shown) through the multireflective cell 32 comprising a 75 μm inner diameter, dimension "a", of the capillary 33. Suitable capillaries can be purchased from Polymicro Technologies, Inc., Phoenix, Ariz. A polyimide sleeve, not shown, protects the capillary 33. The multireflective cell 32 is formed by first burning away 1 cm of the polyimide sleeve.

A layer of silver 36 is deposited on the capillary 33 (where the polyimide sleeve has been burned away) by redox reaction of $Ag(NH_3)_2^+$ and glucose. This silver layer 36 forms a reflecting mirror. A layer of black paint 38 is then applied over the silver layer 36 in order to help protect the multireflective cell 32 from physical damage.

Incident and exit light windows 40 and 42, separated by distance D1 (0.8 mm), are created adjacent the capillary 33 by scraping, etching or other suitable techniques known in the art. Dimension D2 represents the distance between the outermost extremities of the windows 40 and 42. The cell volume, calculated from dimension D2, is 6.6 nl in the preferred embodiment.

The sensitivity of the multireflective cell 32 can be enhanced further by increasing the distance D1 between the two windows 40 and 42. In order to avoid too much loss in efficiency, dimension D1 should not be greater than 1.0 mm. A longer distance, coupled with more reflections, also reduces the output light intensity exiting the capillary 33, due to loss of light power during reflection. At very great distances, the output light intensity will be lower than the detector noise, resulting in no detectable signal.

Figure 3:
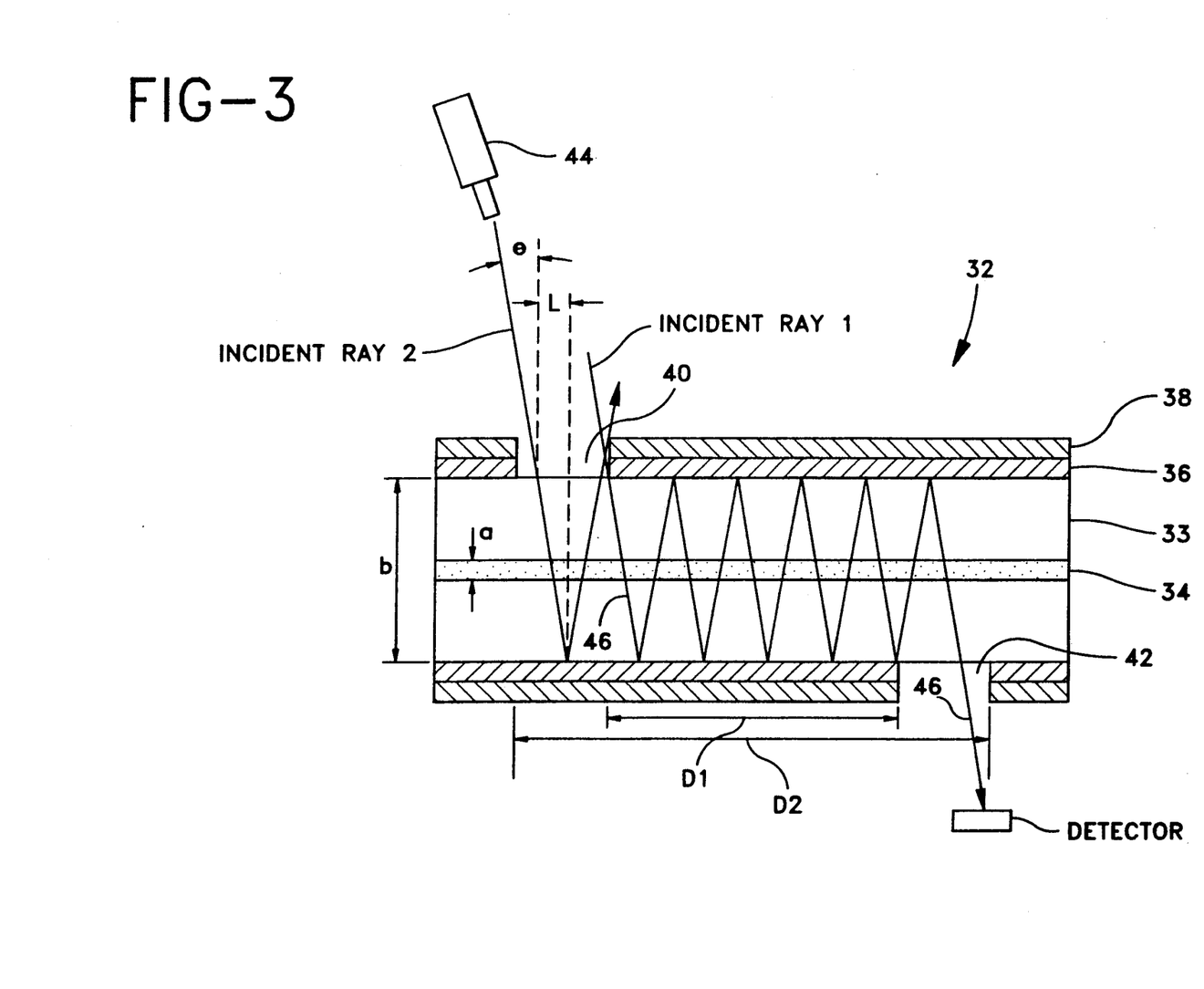
FIG. 3 is a cross-sectional view of the cell in accordance with FIG. 2, which shows the path of electromagnetic radiation.

Referring now also to FIG. 3, a cross-sectional view of the multireflective cell 32 is shown. A laser 44 fires a beam of light; its path is depicted as reference numeral 46. The optimal number of light reflections for the multireflection cell 32 depends on the incident light power, the reflectivity of the silver mirror coating 36.

In order to obtain higher output light intensity at the exit window 42, the axial length of the incident window 40 should not be less than 2 L, which equals:

$$2L = 2 \cdot b \cdot \tan \theta$$

where b is the outer diameter of the capillary 33 and $\theta$ is the angle of the light beam 46 as it enters the incident window 40, relative to the plane which is perpendicular to the longitudinal axis of the capillary 33. The optimal angle $\theta$ is between 5 and 7 degrees. Therefore, the axial length for the preferred embodiment, which allows the maximum amount of light to enter the capillary 33, is between 0.05-0.1 mm.

According to the theory of radial reflection, the rays of light 46 which do not pass the inner diameter, dimension a, of the capillary 33 during the first segment of travel therein (because their incident positions are too far away from the center of the capillary 33) will never pass the inner diameter, dimension "a", in their entire travel. Hence, the rays of light make no contribution to absorption by the sample in channel 34. Therefore, in order to cut off useless light, the radial width of the incident window 40 (shown in FIG. 2 as dimension "h") should be equal to or slightly less than the inner diameter, dimension "a", of the capillary 33.

A ray of light 46 will rotate after each reflection, with the angle of rotation depending on both the incident position of the ray 46 and the refractive index of each medium 33 and 34. After many reflections, rays 46 will be distributed around the entire circumference of the capillary 33. Therefore, the exit window 42 should be ring-shaped, ideally.

Figure 4A:
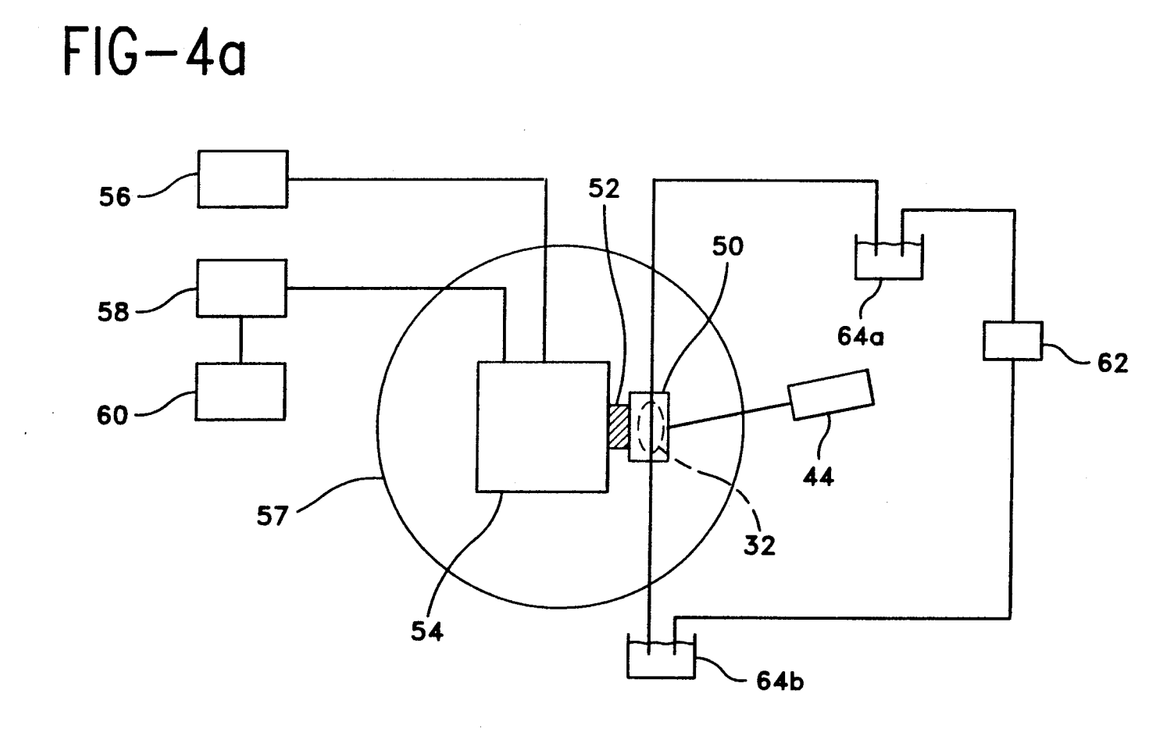
FIGS. 4a and 4b are schematic views of the inventive system, showing an enlarged view of the incorporated multireflective cell.
Figure 4B:
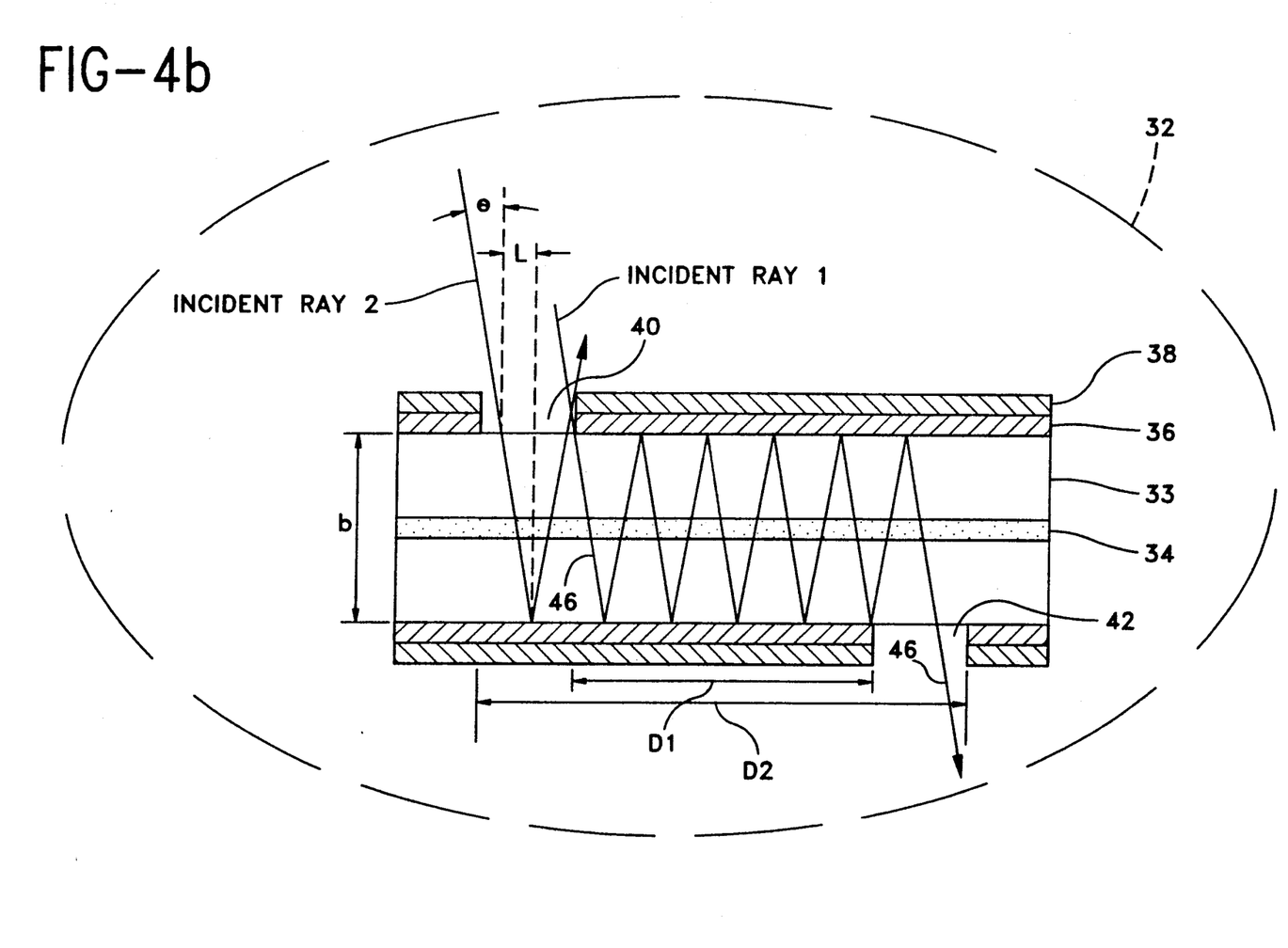

Referring now to FIGS. 4a and 4b, a schematic diagram of the system in the preferred embodiment is shown. The multireflective cell 32 is incorporated in the system. The light source is a 5 mW He-Ne laser 44 (Model 1105P, Uniphase, Sunnyvale, Calif.). The multireflective cell 32 is mounted on a conventional cell 50. The conventional cell 50 and a 632.8 nm interference filter 52 (Corion Corp., Holliston, Mass.) are taped on the window (not shown) of a photomultiplier tube 54 (Model No. R928, Hamamatsu, Somerset, N.J.). The entire assembly (32, 50, 52 and 54) is then mounted on a rotary stage 57 which allows for fine adjustment of the incident angle $\theta$ (FIG. 4b).

In operation, the laser beam 46 first passes through the aperture (60 μm × 1.4 mm), not shown, of the conventional cell 50, then strikes the incident window 40 of the multireflective cell 32. The intensity of the light exiting the exit window 42 is detected by a photomultiplier tube 54. The preferred embodiment incorporates a ring-shaped photodetector (not shown) in order to collect the entire light output. The photomultiplier tube 54 is connected to either a Keithley 177 digital multimeter 56 (in static measurement) or an Oriel 7072 detection system 58 and an OmniScribe A5111-5 chart recorder 60 (in CZE running). A high-voltage power supply 62 is used to drive the electrophoresis of the CZE system. A buffer 64a contains the fluid sample (not shown). A reservoir 64b accumulates the fluid as it exits the capillary 33.

Figure 5:
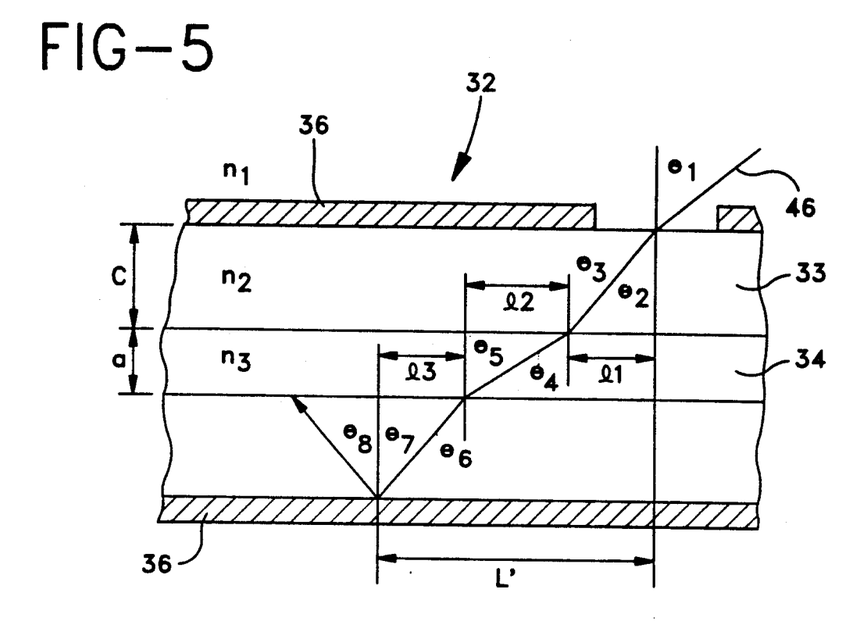
FIG. 5 is a diagrammatic view of a ray tracing of axial reflection.

Referring now to FIG. 5, a cross-section of the multireflective cell 33 is shown, demonstrating the refraction and axial reflection that occur when light 46 passes through the fluid sample in channel 34. When a light ray 46 impinges on a reflective surface, reflection will take place. The reflection angle is equal to the incident angle. When a light ray 46 crosses from a first medium to a second medium, refraction will occur. The refraction angle follows Snell's law:

$$n_1 \sin \theta_1 = n_2 \sin \theta_2$$

where $\theta_1$ and $\theta_2$ are the incident and refraction angle, respectively, and $n_1$ and $n_2$ are the refractive indices of the first and second media, respectively. Typical refractive indices of the media include $n_1$(air) = 1.000, $n_2$(silica) = 1.458, and $n_3$(water) = 1.333.

Axial reflection is explained mathematically:

$$\theta_2 = a\text{-sin}[(n_1 \sin \theta_1)/n_2]$$

From trigonometry, $l_1 = c \tan \theta_2$ and $\theta_3 = \theta_2$.

Similarly, $l_2$ and $l_3$ can be obtained. Then, the total length "L'" that the ray 46 travels is represented by:

$$L' = l_1 + l_2 + l_3$$

In the current cell design, the exterior of the capillary 33 is silver-mirrored, as aforementioned. When the ray 46 strikes the silver coating 36, it will be reflected with $\theta_8 = \theta_7$; the tracing will follow a path symmetrical with the pattern established above. Taking symmetry into account, the distance the ray 46 travels with each reflection is L'. After traveling a distance S along the axis of a capillary 33, the number of reflections will be:

$$N = S/L' - 1$$

N also indicates the factor by which the path length was increased.

Figure 6:
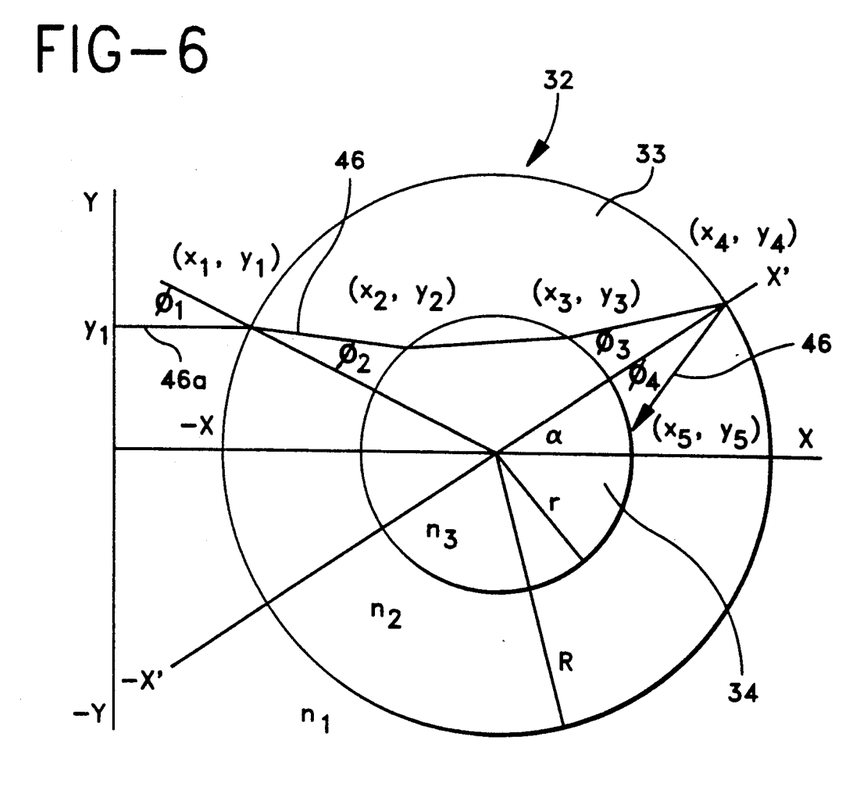
FIG. 6 is a diagrammatic view of a ray tracing of radial reflection.

Referring now to FIG. 6, radial reflection in the multireflective cell 32 is shown. For a multireflective cell 32 with a capillary 33 that is cylindrical, the path of light 46 will be reflected radially as well as axially.

An incident ray 46a is assumed to be parallel to the X-axis; its position is $y_1$. According to trigonometry, coordinate $x_1$ will be:

$$x_1 = -(R^2 - y_1^2)^{0.5}$$

When the ray reflects at point $(x_4, y_4)$, it is obvious that:

$$\theta_4 = \theta_3$$

The ray tracings before and after reflection are symmetric along the X'-axis, which is rotated by an angle of $\alpha$ with regard to the X-axis. The angle $\alpha$ depends on both the incident position $(x_1, y_1)$ of the ray 46a and the refractive indices $n_1$, $n_2$ and $n_3$ of each medium (air, silica and water, respectively).

Since the ray tracing is symmetric along the X'-axis, further coordinates such as $(x_5, y_5)$ can be established. First, convert $(x_3, y_3)$ to $(x_3', y_3')$ as follows:

$$x_3' = x_3 \cos(\alpha) + y_3 \sin(\alpha)$$

$$y_3' = -x_3 \sin(\alpha) + y_3 \cos(\alpha)$$

The coordinates $(x_5', y_5')$ will be:

$$x_5' = x_3' \quad y_5' = -y_3'$$

Secondly, convert $(x_5', y_5')$ to $(x_5, y_5)$ as follows:

$$x_5 = x_5' \cos(\alpha) - y_5' \sin(\alpha)$$

$$y_5 = x_5' \sin(\alpha) + y_5' \cos(\alpha)$$

Figure 7A:
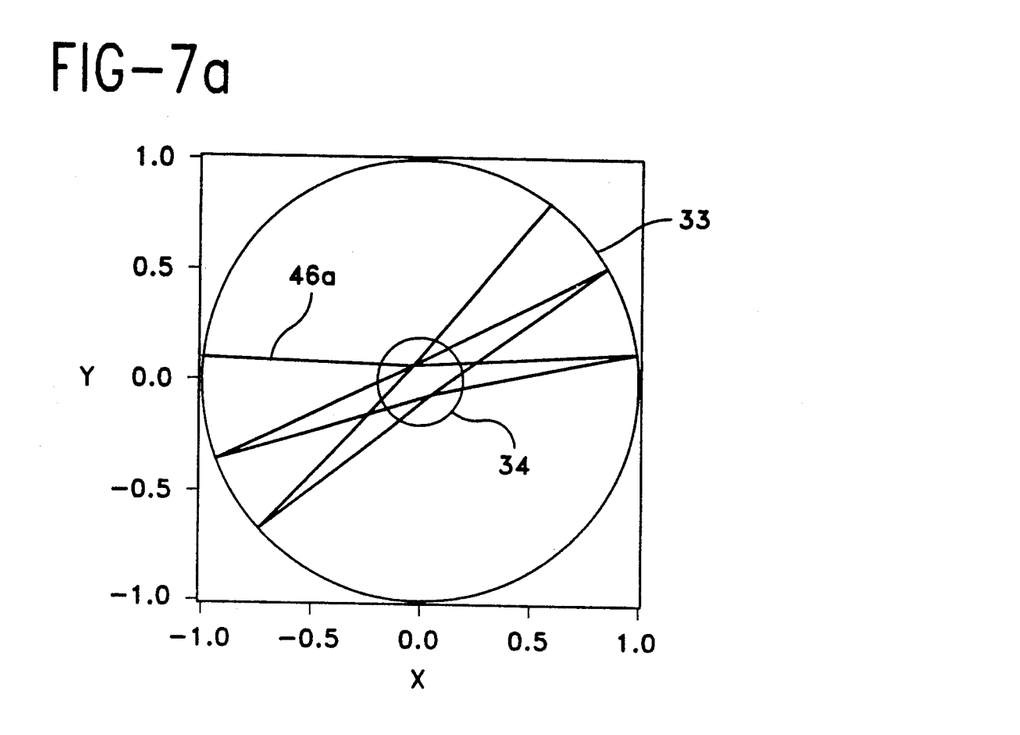
FIGS. 7a and 7b are diagrammatic views, respectively, of a ray tracing after four reflections in a multireflective cell using incident position $y_1 = 0.10$ and incident position $y_1 = 0.20$.
Figure 7B:
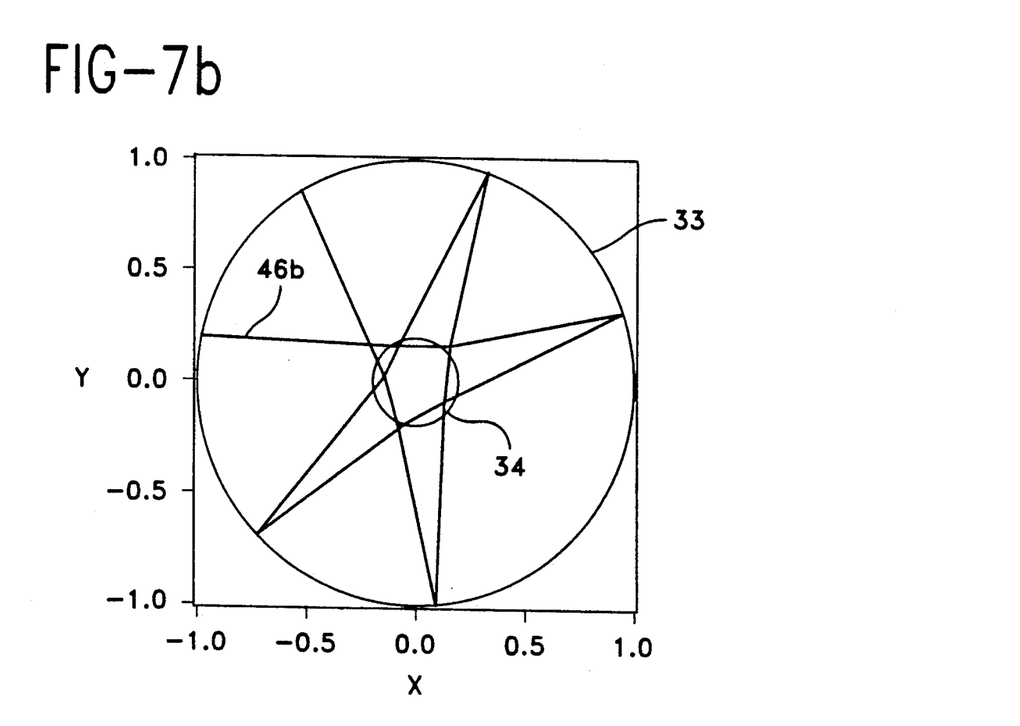

Referring now to FIGS. 7a and 7b, two typical ray tracings of radial reflection after four reflections in the multireflective cell 32 are shown. In FIG. 7a, the light beam 46a enters the cell 32 at Y = 0.1. In FIG. 7b, the light beam 46b enters the cell 32 at Y = 0.2.

Figure 8:
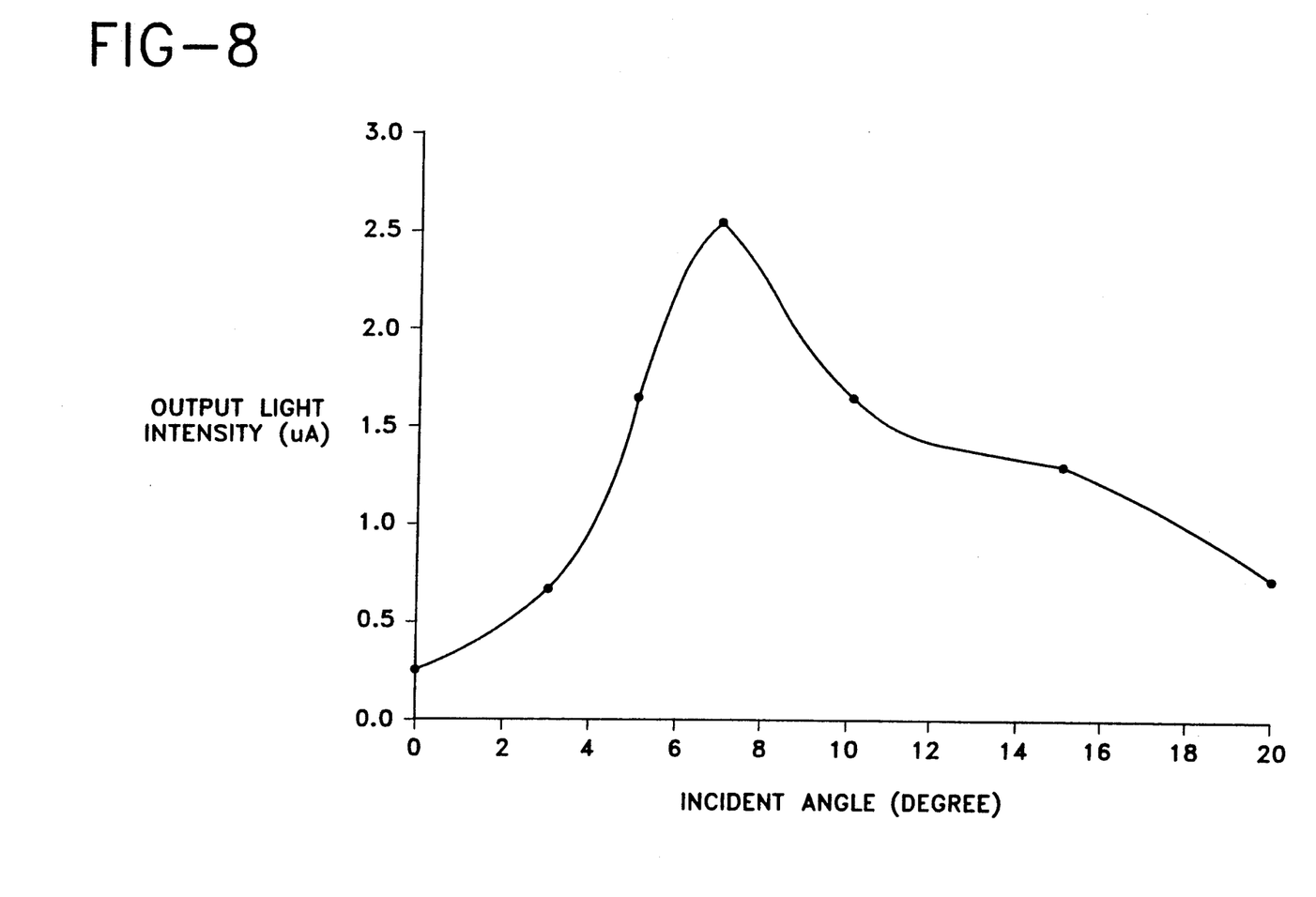
FIG. 8 is a graph depicting the relationship of the incident angle to output light intensity.

Referring now to FIG. 8, the relationship of output light intensity to incident angle $\theta$ is shown. When $\theta \approx 0$, the light intensity is very low (only 10% of the maximal intensity). The incident angle $\theta$ is a critical parameter because it affects the light intensity arriving at the photodetector and controls the number of reflections in the capillary, thus affecting detection sensitivity. The output light intensity quickly increases by increasing $\theta$ from 0 to 7 degrees (with a maximum intensity at 7 degrees), then slowly decreases with increasing $\theta$.

Figure 9:
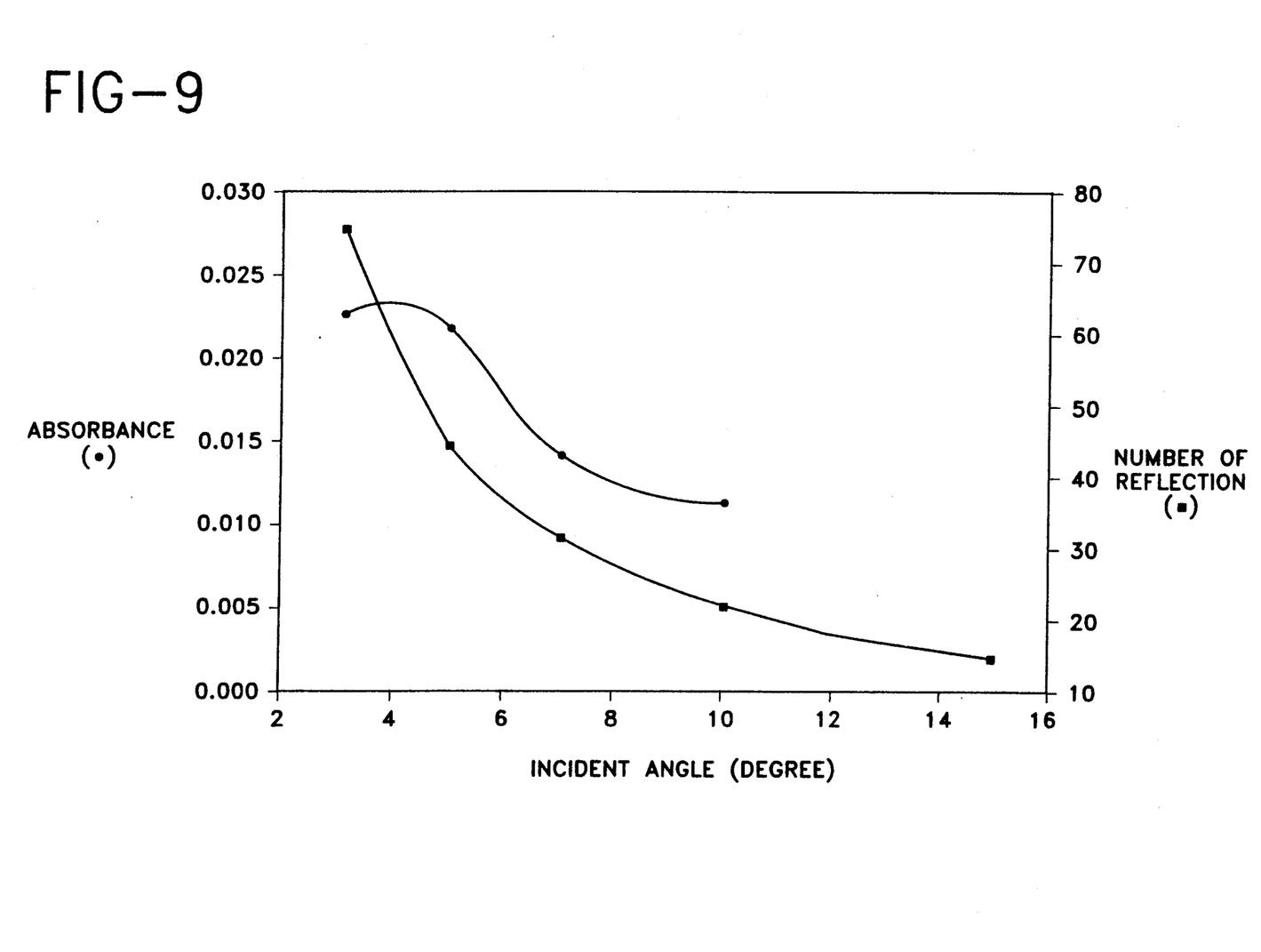
FIG. 9 is a graph depicting the relationship of the incident angle to the number of reflections and to absorbance.

Referring now to FIG. 9, the relationships of $\theta$ to the number of reflections and to absorbance, or sensitivity, are shown. In theory, the sensitivity of a multireflective cell is proportional to the number of reflections. Reducing incident angle will increase the number of reflections. Therefore, decreasing the incident angle $\theta$ will enhance sensitivity. This appears to be true for $\theta$ in the range of 5 to 10 degrees. However, such a relationship does not hold at smaller incident angles. When $\theta$ is reduced from 5 to 3 degrees, the calculated number of reflections increases from 44 to 74, which means that the path length will be increased approximately 1.7 times. However, the absorbance increased only 2.8% experimentally. The loss of light intensity was approximately 60%. Therefore, an incident angle $\theta$ of 5 degrees is optimal.

Figure 10:
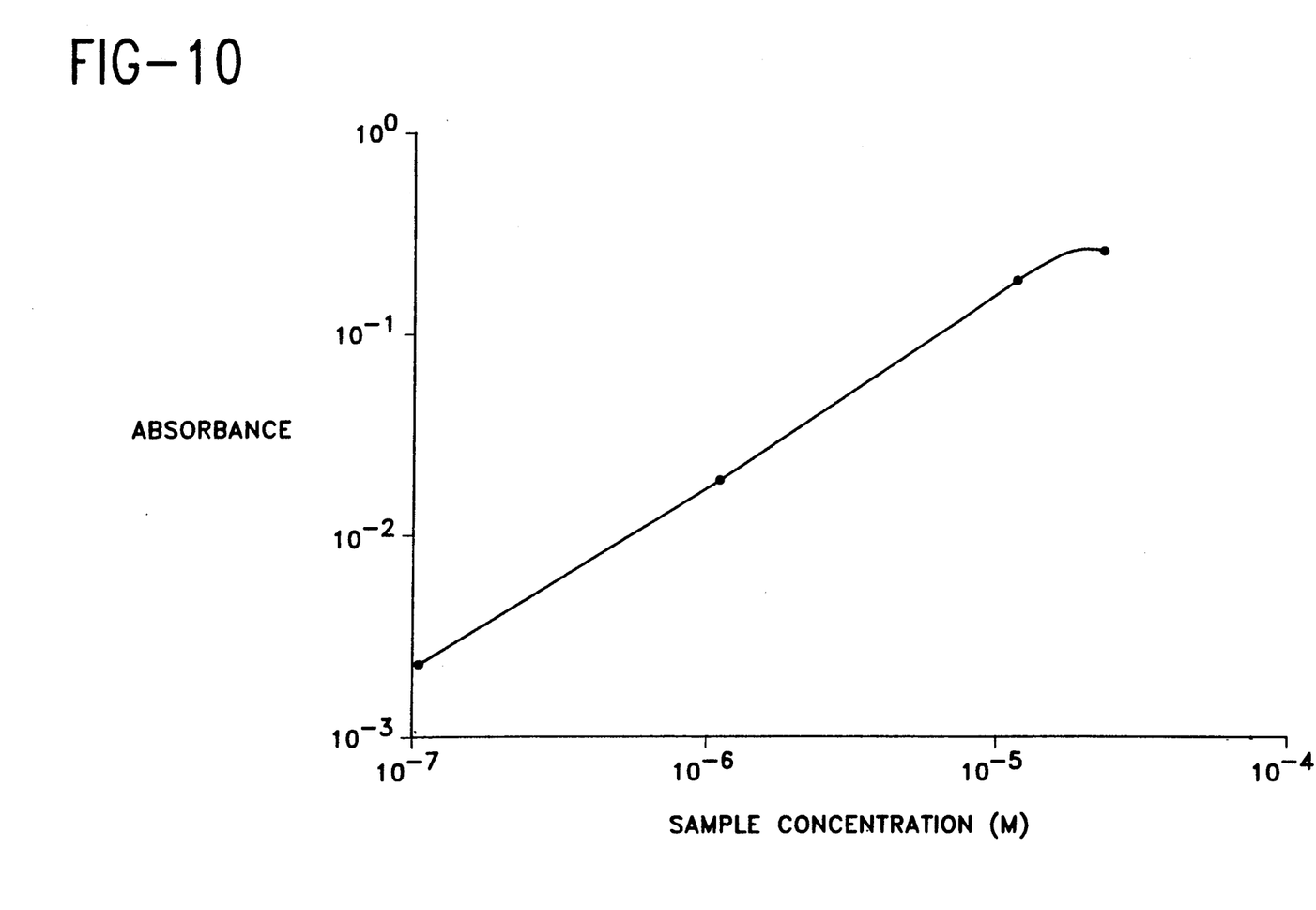
FIG. 10 is a graph depicting the linear dynamic range of detection with the multireflective cell.

Referring now to FIG. 10, there is shown the linear dynamic range and detection limit of the system when a substance called "brilliant green" is analyzed. The linear dynamic range of the multireflective cell was examined by static measurement with $\theta = 5$ degrees. The linearity established from FIG. 8 is two orders of magnitude, from 0.2 to 0.002 absorbance units. With the sample remaining stationary with respect to the capillary, noise is about $4.3 \times 10^{-4}$ au, and the absorbance of $1.1 \times 10^{-7}$M brilliant green is 0.0022 au. The calculated detection limit (signal to noise ratio=3) is $6.5 \times 10^{-8}$M. Although brilliant green has a high molar absorptivity ($\epsilon = 8.2 \times 10^4$ at 633 nm and pH 5.6), such a detection limit is still significant. When applied to actual CZE separations, the calculated concentration limit of detection was increased to $3.0 \times 10^{-7}$M, because of band dispersion and increased noise levels.

Figure 11A:
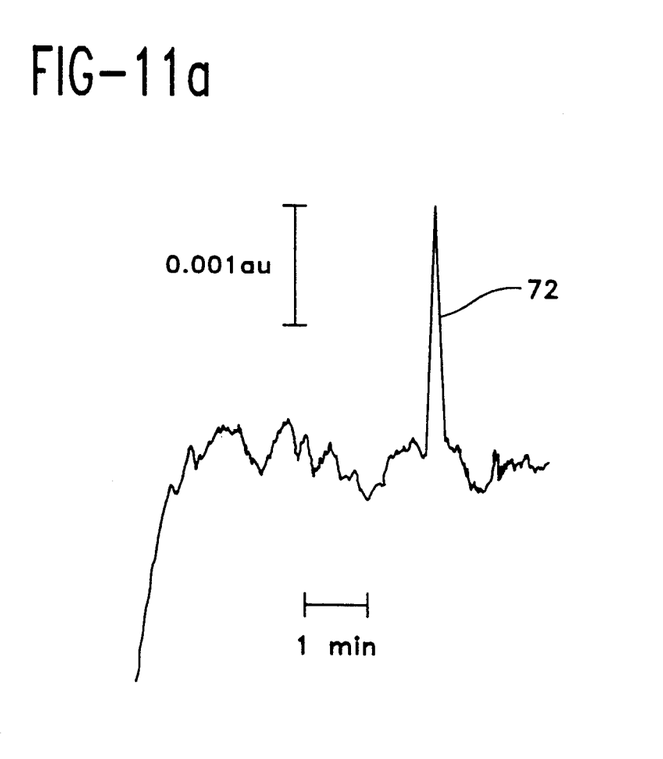
FIGS. 11a and 11b are electrophoretograms of brilliant green obtained from a single-pass cell and from a multireflective cell, respectively.
Figure 11B:
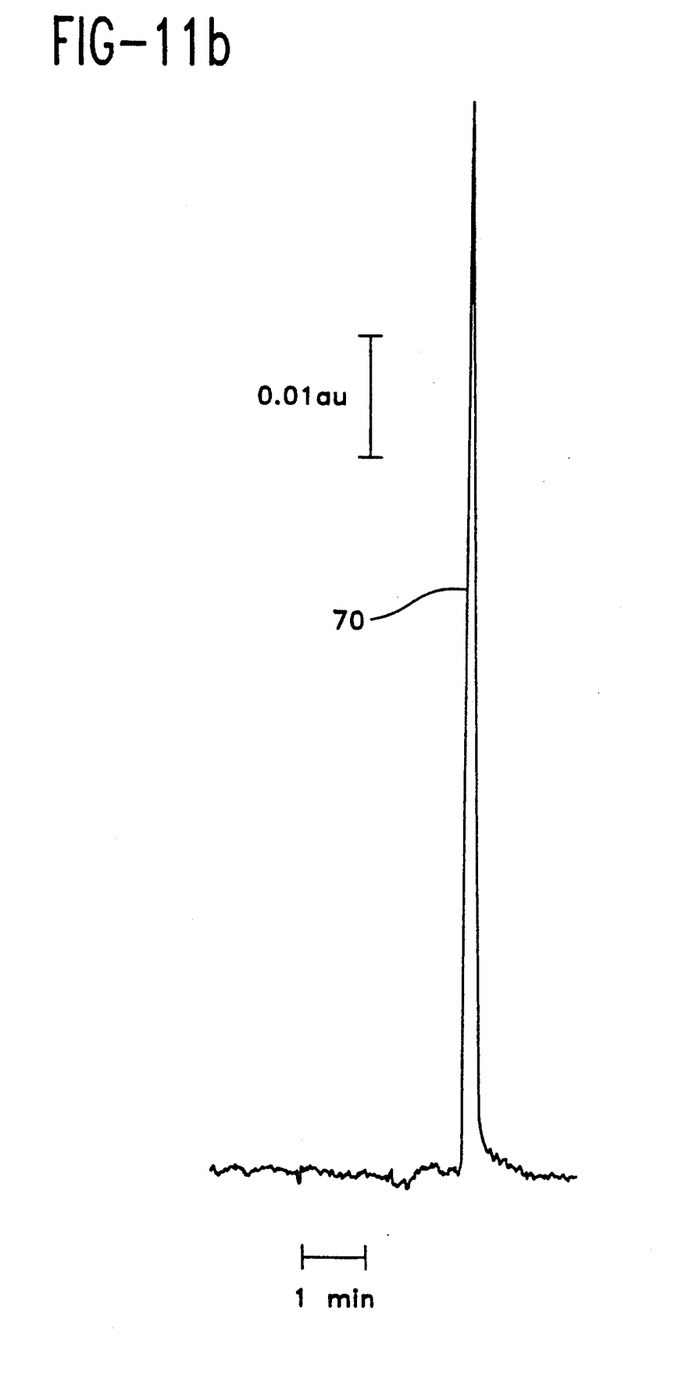

Referring now to FIGS. 11a and 11b, there are shown actual electrophoretograms, the results of a single-pass cell and a multireflective cell performing CZE on brilliant green. The multireflective cell is characterized by improved sensitivity when compared with conventional single-pass cells, and with no increase in cell volume. The peak sensitivity 70 of the multireflective cell is over 40 times higher than the peak sensitivity 72 of a single-pass cell. Noise levels were similar for both cells. The statistical results are shown in the table below. These results agree with theoretical calculations.

TABLE I

Performance Comparison of Multireflective Cell to Single-pass Cell

| CONDITION | ABSORBANCE* | | |
|---|---|---|---|
| | Multireflective | Single | Ratio |
| static measurement | 0.230 | 0.0055 | 41.8 |
| static noise | $4 \times 10^{-4}$ | $4 \times 10^{-4}$ | |
| CZE measurement | 0.0899 | 0.0022 | 40.9 |
| CZE noise | $8.3 \times 10^{-4}$ | $6.6 \times 10^{-4}$ | |

*$1.1 \times 10^{-5}$ M brilliant green ($\theta = 5$)

Since other modifications and changes varied to fit particular operating requirements and environments will be apparent to those skilled in the art, the invention is not considered limited to the examples chosen for purposes of disclosure, and covers all changes and modifications which do not constitute departures from the true spirit and scope of this invention.

What is claimed is:

1. A multireflective cell for use in capillary zone electrophoresis (CZE), and capable of analyzing fluids with concentrations being approximately below $10^{-6}$M, comprising:
   a) a capillary having a longitudinal axis, an outer surface and an inner surface defining a channel disposed therein for receiving a fluid sample to be analyzed, said capillary having an incident window for allowing said electromagnetic energy to enter said capillary and an exit window for allowing said electromagnetic energy to exit said capillary, said incident window and said exit window being open to said fluid sample and spaced apart from each other along said longitudinal axis, so that said electromagnetic energy that enters said capillary is internally passed through said fluid sample and exits said capillary, said capillary having an outer diameter of approximately less than 1 mm, and an inner diameter defining said channel of approximately less than 0.1 mm for supporting a fluid to be analyzed;
   b) reflective means defining a reflective surface disposed on said outer surface of said capillary for reflecting electromagnetic energy passing through said fluid sample a number of times before said energy exits from said exit window of said capillary; and
   c) a source of high electromotive force for driving said fluid sample through said capillary.

2. The multireflective cell in accordance with claim 1 wherein the cross-section of said capillary is substantially circular and symmetrical about its longitudinal axis.

3. The multireflective cell in accordance with claim 1 wherein said reflective means comprises a coating.

4. The multireflective cell in accordance with claim 3 wherein said coating comprises metal.

5. The multireflective cell in accordance with claim 3 further comprising a protective layer applied on the outer surface of said reflective means.

6. The multireflective cell in accordance with claim 1 wherein said incident window has an axial length not smaller than 0.05 mm.

7. The multireflective cell in accordance with claim 1 wherein said exit window is disposed downstream of said incident window with respect to the longitudinal axis of said capillary and wherein the on-center distance between said exit window and said incident window along the longitudinal axis of said capillary is not more than 5.0 mm.

8. A method for performing a capillary zone electrophoresis (CZE) process utilizing a multireflective cell, said method comprising the steps of:
   a) directing electromagnetic energy into a multireflective cell, said electromagnetic energy being utilized for analysis of a fluid sample;
   b) passing said fluid sample into said multireflective cell;
   c) performing CZE by moving suspended particles through said fluid sample via an electromotive force and passing said electromagnetic energy into said multireflective cell and through said fluid sample, said electromagnetic energy being partially absorbed thereby; and
   d) reflecting said electromagnetic energy within said multireflective cell, so that said electromagnetic energy passes through said fluid sample a plurality of times and is partially absorbed thereby.

9. The method for performing capillary zone electrophoresis (CZE) utilizing a multireflective cell of claim 8, the steps further comprising:
   e) collecting remaining energy of said electromagnetic energy exiting said multireflective cell.

10. The method for performing capillary zone electrophoresis (CZE) utilizing a multireflective cell of claim 9, the steps further comprising:
   f) determining optimal angle between said electromagnetic energy source and said multireflective cell; and
   g) calculating the number of reflections of said electromagnetic energy within said multireflective cell in order to aid in determining said optimal angle of incidence.

* * * * *